(12) United States Patent
Aoyama

(10) Patent No.: US 12,161,497 B2
(45) Date of Patent: Dec. 10, 2024

(54) MEDICAL IMAGE DISPLAY APPARATUS

(71) Applicant: CANON MEDICAL SYSTEMS CORPORATION, Otawara (JP)

(72) Inventor: Gakuto Aoyama, Nasushiobara (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 602 days.

(21) Appl. No.: 17/473,028

(22) Filed: Sep. 13, 2021

(65) Prior Publication Data
US 2022/0079539 A1 Mar. 17, 2022

(30) Foreign Application Priority Data
Sep. 14, 2020 (JP) .................. 2020-153593

(51) Int. Cl.
*A61B 6/50* (2024.01)
*A61B 6/00* (2006.01)
*A61B 6/03* (2006.01)
*A61B 6/46* (2024.01)

(52) U.S. Cl.
CPC ............ *A61B 6/5205* (2013.01); *A61B 6/032* (2013.01); *A61B 6/466* (2013.01); *A61B 6/469* (2013.01); *A61B 6/503* (2013.01)

(58) Field of Classification Search
CPC ....... A61B 6/5205; A61B 6/032; A61B 6/466; A61B 6/469; A61B 6/503; A61B 6/5211
See application file for complete search history.

(56) References Cited

U.S. PATENT DOCUMENTS

| | | | |
|---|---|---|---|
| 9,886,781 B2 | 2/2018 | Goto | |
| 2008/0077032 A1* | 3/2008 | Holmes | A61B 8/00 600/523 |
| 2013/0205247 A1 | 8/2013 | Erhard et al. | |
| 2014/0228687 A1 | 8/2014 | Park et al. | |
| 2015/0348263 A1 | 12/2015 | Yamamori et al. | |
| 2016/0012614 A1 | 1/2016 | Goto | |
| 2017/0301091 A1 | 10/2017 | Nakagomi | |

(Continued)

FOREIGN PATENT DOCUMENTS

| | | |
|---|---|---|
| JP | 2000-287962 A | 10/2000 |
| JP | 2004-159913 A | 6/2004 |

(Continued)

OTHER PUBLICATIONS

Japanese Office Action issued Mar. 5, 2024 in Japanese Application 2020-153593, 3 pages.

(Continued)

*Primary Examiner* — Fayyaz Alam
(74) *Attorney, Agent, or Firm* — Oblon, McClelland, Maier & Neustadt, L.L.P.

(57) ABSTRACT

A medical image display apparatus according to an embodiment includes processing circuitry. The processing circuitry is configured to obtain an image data set of volume data or image data at multiple points in time. The processing circuitry is configured to specify an image of interest indicating an observation cross-sectional plane from the image data set. The processing circuitry is configured to specify a region of interest on the basis of the image data set. The processing circuitry is configured to cause the image of interest and information about the region of interest to be displayed.

18 Claims, 14 Drawing Sheets

(56) References Cited

U.S. PATENT DOCUMENTS

| | | | |
|---|---|---|---|
| 2023/0038493 A1* | 2/2023 | Villongco | A61B 5/0275 |
| 2023/0320679 A1* | 10/2023 | Yuzawa | A61B 6/463 |
| 2023/0401709 A1* | 12/2023 | Sasuga | A61B 6/5217 |
| 2024/0020838 A1* | 1/2024 | Takei | A61B 6/463 |

FOREIGN PATENT DOCUMENTS

| | | |
|---|---|---|
| JP | 2004-180932 A | 7/2004 |
| JP | 2012-16480 A | 1/2012 |
| JP | 2012-176282 A | 9/2012 |
| JP | 2013-544559 A | 12/2013 |
| JP | 2014-151208 A | 8/2014 |
| JP | 2015-071032 A | 4/2015 |
| JP | 2015-226693 A | 12/2015 |
| JP | 2017-189384 A | 10/2017 |
| WO | WO 2014/132829 A1 | 9/2014 |

OTHER PUBLICATIONS

Office Action issued Aug. 7, 2024, in corresponding Japanese Patent Application No. 2020-153593, 4 pages.

* cited by examiner

FIG.11

REGION(S) OF INTEREST SATISFYING THE  ☑ DISPLAYED
FOLLOWING CONDITIONS SHOULD BE
                                    ☐ NOT DISPLAYED

☑ DISTANCE FROM OBSERVATION CROSS-SECTIONAL PLANE    [ 5 ]   OR LESS SLICES

☑ PIXEL VALUE (A TOTAL WHEN THERE ARE MORE THAN ONE)   [ 500 ]   HU OR HIGHER

☐ NUMBER OF REGIONS OF INTEREST   [    ]   OR MORE

S3 IN T3

MEDICAL IMAGE DISPLAY APPARATUS

CROSS-REFERENCE TO RELATED APPLICATIONS

This application is based upon and claims the benefit of priority from Japanese Patent Application No. 2020-153593, filed on Sep. 14, 2020; the entire contents of which are incorporated herein by reference.

FIELD

Embodiments described herein relate generally to a medical image display apparatus.

BACKGROUND

In recent years, as a technique for assisting surgery planning related to heart valves, a method has been proposed by which a distribution of calcification in a heart valve is calculated from an image of the examined subject so as to calculate a degree of difficulty of replacement with an artificial valve. According to this method, a user such as a medical doctor recognizes the position and the amount of the calcification from an observation cross-sectional plane of the heart valve and estimates an opening amount of the artificial valve. Because the valve has a three-dimensional shape, however, it is difficult to recognize the calcification as a whole only from the observation cross-sectional plane, and the estimate may be inaccurate in some situations.

This problem not only arises during surgery planning related to heart valves, but may also similarly arise during surgery planning related to other anatomical structures.

BRIEF DESCRIPTION OF THE DRAWINGS

FIG. 11 is a drawing illustrating an example of a setting-purpose screen displayed by the display controlling function according to the first modification example of the first embodiment;

DETAILED DESCRIPTION

A medical image display apparatus according to an embodiment includes an obtaining unit, a first specifying unit, a second specifying unit, and a display controlling unit. The obtaining unit is configured to obtain an image data set of volume data or image data at multiple points in time. The first specifying unit is configured to specify an image of interest indicating an observation cross-sectional plane from the image data set. The second specifying unit is configured to specify a region of interest on the basis of the image data set. The display controlling unit is configured to cause the image of interest and information about the region of interest to be displayed.

The following will describe exemplary embodiments of the medical image display apparatus in detail, with reference to the accompanying drawings.

First Embodiment

Figure 1:
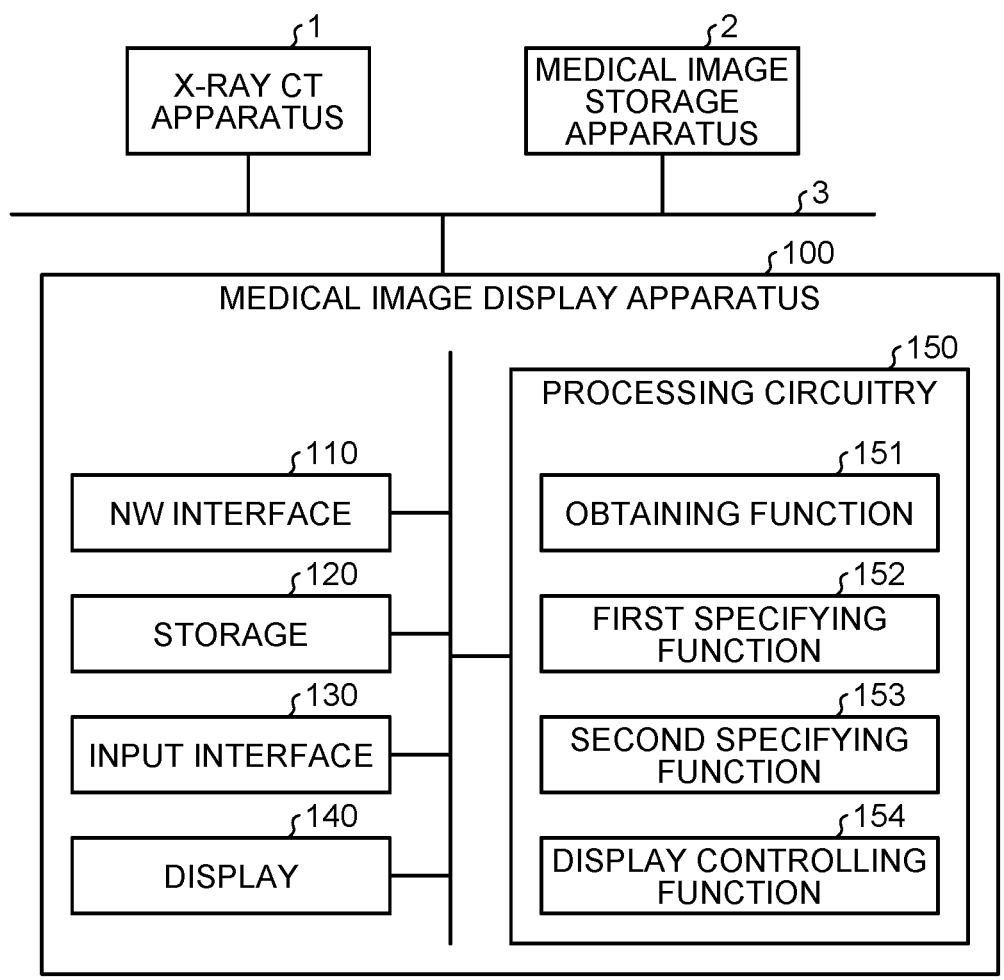
FIG. 1 is a diagram illustrating an exemplary configuration of a medical image display apparatus according to a first embodiment.

FIG. 1 is a diagram illustrating an exemplary configuration of a medical image display apparatus according to a first embodiment.

For example, as illustrated in FIG. 1, a medical image display apparatus 100 according to the present embodiment is communicably connected to an X-ray Computed Tomography (CT) apparatus 1 and to a medical image storage apparatus 2, via a network 3.

In addition to the X-ray CT apparatus 1, the medical image display apparatus 100 may further be connected to other medical image diagnosis apparatuses such as a Magnetic Resonance Imaging (MRI) apparatus, an ultrasound diagnosis apparatus, a Positron Emission Tomography (PET) apparatus, a Single Photon Emission Computed Tomography (SPECT) apparatus, and/or the like.

The X-ray CT apparatus 1 is configured to generate a CT image related to an examined subject (hereinafter, "patient"). More specifically, the X-ray CT apparatus 1 is configured to acquire projection data expressing a distribution of X-rays that have passed through the patient, by moving an X-ray tube and an X-ray detector to turn on a circular trajectory around the patient. Further, on the basis of the acquired projection data, the X-ray CT apparatus 1 generates the CT image.

The medical image storage apparatus 2 is configured to store therein various types of medical images related to the patient. More specifically, the medical image storage apparatus 2 is configured to obtain the CT image from the X-ray CT apparatus 1 via the network 3 and to save and store the CT image in a storage therein. For example, the medical image storage apparatus 2 may be realized by using a computer device such as a server or a workstation. Alternatively, for example, the medical image storage apparatus 2 may be realized by using a Picture Archiving and Communication System (PACS) or the like so as to store the CT image therein in a format compliant with Digital Imaging and Communications in Medicine (DICOM).

The medical image display apparatus 100 is configured to display various types of images related to the patient. More specifically, the medical image display apparatus 100 is configured to obtain the CT image from either the X-ray CT apparatus 1 or the medical image storage apparatus 2 via the network 3 and to display the CT image and various types of information obtained from the CT image. For example, the medical image display apparatus 100 is realized by using a compute device such as a server or a workstation.

For example, the medical image display apparatus 100 includes a network (NW) interface 110, a storage 120, an input interface 130, a display 140, and processing circuitry 150.

The NW interface 110 is configured to control communication and transfer of various types of data transmitted and received between the medical image display apparatus 100 and the other apparatuses connected via the network 3. More specifically, the NW interface 110 is connected to the processing circuitry 150 and is configured to transmit the data received from the other apparatuses to the processing circuitry 150 and to transmit the data received from the processing circuitry 150 to any of the other apparatuses. For example, the NW interface 110 is realized by using a network card, a network adaptor, a Network Interface Controller (NIC), or the like.

The storage 120 is configured to store therein various types of data and various types of programs. More specifically, the storage 120 is connected to the processing circuitry 150 and is configured to store therein the data received from the processing circuitry 150 and to read and transmit any of the stored data to the processing circuitry 150. For example, the storage 120 is realized by using a semiconductor memory element such as a Random Access Memory (RAM) or a flash memory, or a hard disk, an optical disk, or the like.

The input interface 130 is configured to receive operations to input various types of instructions and various types of information from a user. More specifically, the input interface 130 is connected to the processing circuitry 150 and is configured to convert the input operations received from the user into electrical signals and to transmit the electrical signals to the processing circuitry 150. For example, the input interface 130 is realized by using a trackball, a switch button, a mouse, a keyboard, a touchpad on which input operations can be performed by touching an operation surface thereof, a touch screen in which a display screen and a touchpad are integrally formed, a contactless input interface using an optical sensor, an audio input interface, and/or the like. In the present disclosure, the input interface 130 does not necessarily have to include one or more physical operation component parts such as a mouse, a keyboard, and/or the like. Possible examples of the input interface 130 include, for instance, electrical signal processing circuitry configured to receive electrical signals corresponding to input operations from an external input device provided separately from the device and to transmit the electrical signals to controlling circuitry.

The display 140 is configured to display various types of information and various types of data. More specifically, the display 140 is connected to the processing circuitry 150 and is configured to display the various types of information and the various types of data received from the processing circuitry 150. For example, the display 140 is realized by using a liquid crystal monitor, a Cathode Ray Tube (CRT) monitor, a touch panel, or the like.

The processing circuitry 150 is configured to control the entirety of the medical image display apparatus 100. For example, the processing circuitry 150 is configured to perform various types of processes in accordance with the input operations received from the user via the input interface 130. Further, for example, the processing circuitry 150 is configured to receive data transmitted from any of the other apparatuses through the NW interface 110 and to store the received data into the storage 120. Further, for example, the processing circuitry 150 is configured to transmit data received from the storage 120 to the NW interface 110, so as to transmit the data to any of the other apparatuses. Further, for example, the processing circuitry 150 is configured to cause the display 140 to display data received from the storage 120.

The exemplary configuration of the medical image display apparatus 100 according to the present embodiment has thus been explained. The medical image display apparatus 100 according to the present embodiment structured as described above is, for example, installed in a medical facility such as a hospital or a clinic and is configured to assist a process of making a surgery plan performed the user such as a medical doctor.

For example, the medical image display apparatus 100 according to the present embodiment is used at the time of making a surgery plan related to a heart valve.

For example, as a treatment method for a patient having a valvular disease, a method is known by which an artificial valve to be a replacement is delivered to the position of a valve to be treated, through a blood vessel (hereinafter, "catheter surgery"). In such catheter surgery, the artificial valve delivered while being folded with small pleats is spread at the position of the valve being treated, so as to replace the valve. Consequently, for such catheter surgery, it is important to obtain morphological information of the valve prior to the surgery and to estimate the opening amount of the artificial valve.

In this regard, for example, as a technique for assisting the obtainment of the morphological information, a technique is known by which a valve region is automatically extracted from an image so as to automatically calculate predetermined measurement items. According to this technique, although the user such as a medical doctor estimates the opening amount of an artificial valve on the basis of the calculated measurement results, it is difficult to make an accurate estimate when calcification has occurred to the valve. Calcification makes valves hard and prevents valves from opening up to the level of the valve diameter.

To cope with this situation, for example, as a technique for assisting surgery planning related to heart valves, another method has been proposed by which a distribution of calcification in a heart valve is calculated from an image of the patient, so as to calculate a degree of difficulty of replacement with an artificial valve. According to this method, a user such as a medical doctor recognizes the position and the amount of the calcification from an observation cross-sectional plane of the heart valve and estimates an opening amount of the artificial valve. Because the valve has a three-dimensional shape, however, it is difficult to recognize the calcification as a whole only from the observation cross-sectional plane, and the estimate may be inaccurate in some situations.

This problem not only arises during surgery planning related to heart valves, but may also similarly arise during surgery planning related to other anatomical structures.

In view of the circumstances described above, the medical image display apparatus 100 according to the present embodiment is configured so as to be able to assist the process of making a surgery plan more appropriately.

More specifically, the medical image display apparatus 100 has, as processing functions included in the processing circuitry 150, an obtaining function 151, a first specifying function 152, a second specifying function 153, and a display controlling function 154. In the present example, the obtaining function 151 is an example of the obtaining unit. The first specifying function 152 is an example of the first specifying unit. The second specifying function 153 is an example of the second specifying unit. The display controlling function 154 is an example of the display controlling unit.

The obtaining function 151 is configured to obtain an image data set of volume data of the patient from either the X-ray CT apparatus 1 or the medical image storage apparatus 2, via the NW interface 110. In this situation, the volume data represents the CT image taken by the X-ray CT apparatus 1.

The image data of the volume data obtained by the obtaining function 151 does not necessarily have to be that of a CT image. It is acceptable to use image data of any type as long as the image is of such a type that three-dimensional information of an anatomical structure in question is stored. For example, it is also acceptable to use an image taken by another medical image diagnosis apparatus, such as an ultrasound image taken by an ultrasound diagnosis apparatus, a Magnetic Resonance (MR) image taken by an MRI apparatus, or the like.

Figure 2:
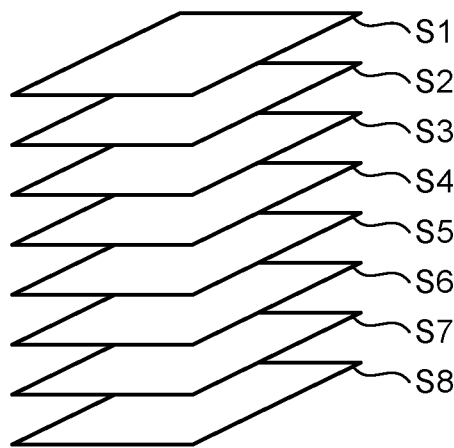
FIG. 2 is a drawing illustrating an example of an image data set of volume data obtained by an obtaining function according to the first embodiment.
Figure 3:
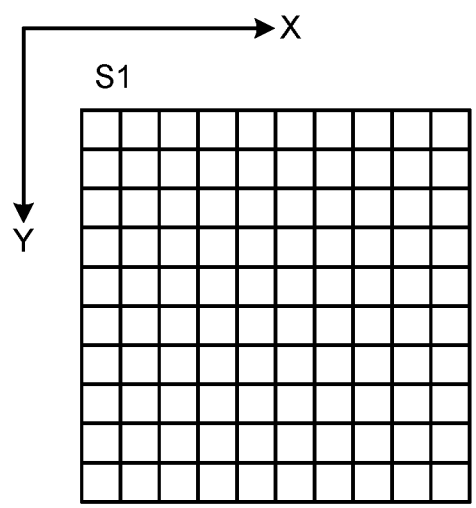
FIG. 3 is another drawing illustrating the example of the image data set of the volume data obtained by the obtaining function according to the first embodiment.

FIGS. 2 and 3 are drawings illustrating an example of the image data set of the volume data obtained by the obtaining function 151 according to the first embodiment.

For example, in the present embodiment, to simplify the explanation, let us discuss an example in which, as illustrated in FIGS. 2 and 3, the obtaining function 151 has obtained the image data set of the volume data including eight slice images S1 to S5 sequentially arranged along the head-to-toe direction, while each of the slice images includes pixels arranged as ten pixels in the X-direction by ten pixels in the Y-direction.

Returning to the description of FIG. 1, the first specifying function 152 is configured to specify an image of interest indicating an observation cross-sectional plane from the image data set of the volume data obtained by the obtaining function 151.

In this situation, the image of interest is represented by image data indicating the observation cross-sectional plane observed by the user and being displayed on a display screen of the display 140, for example. Further, when the display screen of the display 140 is displaying a plurality of pieces of image data, the first specifying function 152 may specify all the pieces of image data as the image of interest or may specify only a part of the image data as the image of interest. For example, when specifying only a part of the image data as the image of interest, the first specifying function 152 may specify, as the image of interest, image data designated by an operation device such as a mouse (e.g., image data displayed in a display region of the display screen in a position where a mouse cursor is present) or may specify, as the image of interest, image data displayed in a display region of the display screen in a line-of-sight position detected by a known line-of-sight detecting device. In this situation, methods that can be used by the first specifying function 152 to specify the image of interest are not limited to the method described above. It is possible to use any method as long as it is possible to specify the image of interest from the image data.

For example, when a surgery plan related to a heart valve is to be made, the first specifying function 152 is configured to specify the image of interest indicating a cross-sectional plane including the heart valve, from the image data set of the volume data.

Further, the first specifying function 152 is configured to further specify an observation region from the image of interest.

For example, when the surgery plan related to the heart valve is to be made, the first specifying function 152 is configured to further specify a region including the heart valve from the image of interest.

In this situation, the observation region denotes a region observed by the user, within the image of interest. The observation region may be the image of interest itself or may be a partial region of the image of interest. When a Partial region is used, the partial region may be a region designated by the user through the input interface 130 or may be a region specified on the basis of a specific algorithm. For example, the observation region may be a region within image of interest that is being displayed in a display region of the display screen or may be specified by using a known image processing technique.

Figure 4:
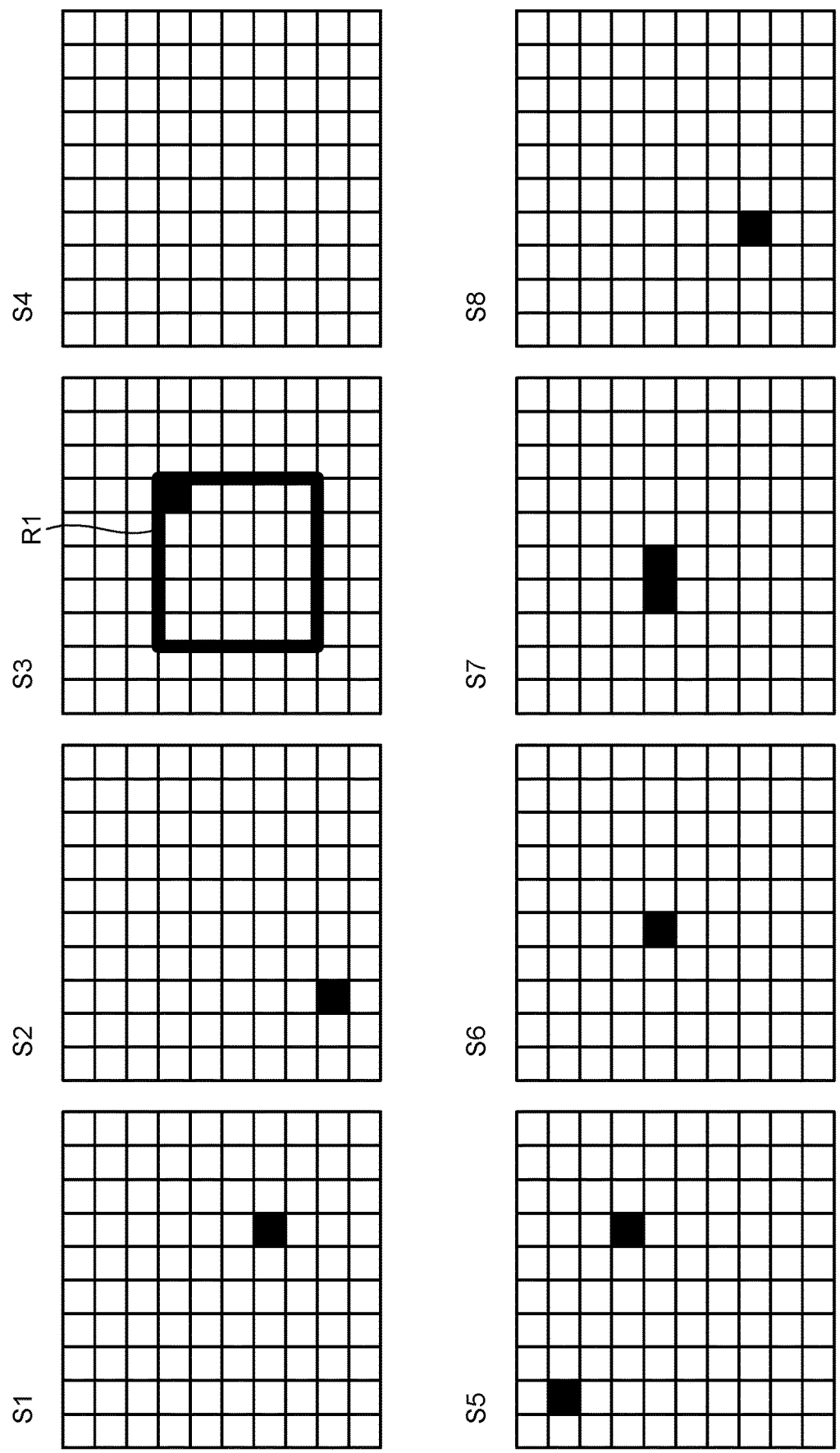
FIG. 4 is a drawing illustrating an example of a process of specifying an image of interest and an observation region performed by a first specifying function according to the first embodiment.

FIG. 4 is a drawing illustrating an example of the process of specifying the image of interest and the observation region performed by the first specifying function 152 according to the first embodiment.

For example, as illustrated in FIG. 4, in the present embodiment, let us assume that the first specifying function 152 has specified the slice image S3 as the image of interest, from the image data set of the volume data illustrated in FIGS. 2 and 3. Further, let us assume that the first specifying function 152 has specified a region corresponding to the range with the X coordinates of 3 to 7 and the range with the Y-coordinates of 4 to 8 in the slice image S3 specified as the image of interest, as an observation region (a region R1 indicated with the bold frame in FIG. 4).

In the present embodiment, an example will be explained in which the image of interest is on the same cross-sectional plane as that of the slice image; however, possible examples of the image of interest are not limited to this example. For instance, the image of interest may be represented by image data of a cross-sectional plane obtained by reconstructing a CT image in an arbitrary direction (through a Multi Planar Reconstruction [MPR]) while using a known technique.

Returning to the description of FIG. 1, the second specifying function 153 is configured to specify a region of interest on the basis of the image data set of the volume data obtained by the obtaining function 151.

In this situation, the region of interest is represented by information about a position within an image occupied by a structure or the like which the user wishes to check on the observation cross-sectional plane. The region of interest may be a two-dimensional region or a three-dimensional region.

In the present embodiment, the second specifying function 153 is configured to specify the region of interest on the basis of data that is included in the image data set of the volume data and corresponds to the observation region specified by the first specifying function 152. In this situation, the second specifying function 153 may specify the region of interest from the data itself corresponding to the observation region or may specify the region of interest from data corresponding to a region (being larger or smaller than the observation region) that is different from the observation region and is specified on the basis of the observation region. However, possible embodiments are not limited to this example, and the second specifying function 153 may specify the region of interest from the entire volume data.

For example, when the surgery plan related to the heart valve is to be made, the second specifying function 153 is configured to specify a calcification region of the heart valve, on the basis of data that is included in the image data set of the volume data and corresponds to a region including the heart valve.

For example, the second specifying function 153 may specify the region of interest, by receiving a designation of the region to serve as the region of interest manually made by the user through a user interface. In another example, the second specifying function 153 may extract (segment) a region on the basis of an anatomical structure rendered in an image by using a known image segmentation technique so as to specify the region as the region of interest. Examples of the known image segmentation technique include a binarization process based on CT values and a graph cut process (Graph Cuts Segmentation).

Methods that can be used by the second specifying function 153 to specify the region of interest are not limited to the example described above. It is acceptable to use any method as long as it is possible to specify a region of interest from the image. For example, the second specifying function 153 may estimate and specify a region of interest from a shape model of the region of interest learned from learning-purpose data in advance by using machine learning technology. Further, for example, with an image segmentation technique such as the binarization process mentioned above, when the process was performed on the entire image, a region other than the structure subject to the process would be specified and there would be a high possibility that that the process at a subsequent stage might be complicated. For this reason, the second specifying function 153 may specify a region (e.g., a heart region or a region in the surroundings the aortic valve, when calcification of the aortic valve is the region of interest) relevant to the region of interest as a relevant region so as to specify the region of interest by performing the process only on the relevant region. In that situation, for example, the second specifying function 153 may specify the relevant region by receiving a designation of the region to serve as the relevant region manually made by the user through a user interface.

For example, in the present embodiment, let us discuss an example in which the second specifying function 153 has specified regions corresponding to the positions of the black pixels in FIG. 4, as regions of interest. In other words, let us assume that the second specifying function 153 has specified, as the regions of interest, nine regions illustrated in FIG. 4 expressed as (7,7,S1), (3,9,S2), (7,4,S3), (2,2,S5), (7,4,S5), (5,5,S6), (4,4,S7), (5,5,S7), and (4,S,S8), where each region is expressed as (X,Y,Z) in an XYZ coordinate system.

The display controlling function 154 is configured to cause the display 140 to display the image of interest specified by the first specifying function 152 and information about the regions of interest specified by the second specifying function 153.

For example, when the surgery plan related to the heart valve is to be made, the display controlling function 154 is configured to cause information about the calcification region of the heart valve to be displayed, as the information about the regions of interest.

Further, in the present embodiment, the display controlling function 154 is configured to cause the information about the regions of interest to be displayed in positions corresponding to the regions of interest within the image of interest.

More specifically, on the basis of a condition set in advance, the display controlling function 154 causes the information about each of the regions of interest to be displayed in a corresponding position in the observation region within the image of interest.

Further, in the present embodiment, the display controlling function 154 is configured to cause the information about the regions of interest to be displayed so as to be superimposed on the image of interest.

More specifically, of the information about the regions of interest, the display controlling function 154 causes information based on a cross-sectional plane or a point in time different from that of the image of interest to be displayed while being projected onto the plane of the image of interest.

For example, of the information about the regions of interest, the display controlling function 154 causes the information based on the cross-sectional plane or the point in time different from that of the image of interest to be displayed while being perpendicularly projected onto the plane of the image of interest.

Figure 5:
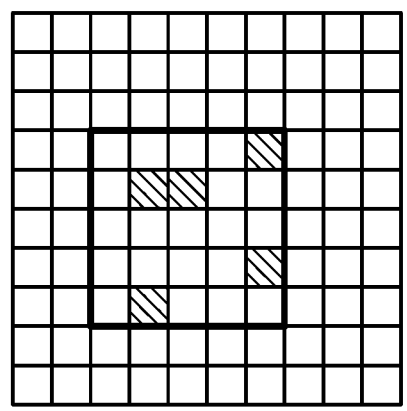
FIG. 5 is a drawing illustrating an example of a process of displaying information about regions of interest performed by a display controlling function according to the first embodiment.
Figure 6:
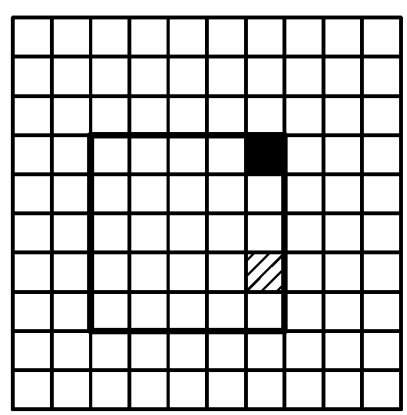
FIG. 6 is a drawing illustrating another example of the process of displaying the information about the regions of interest performed by the display controlling function according to the first embodiment.

FIGS. 5 and 6 are drawings illustrating examples of the process of displaying the information about the regions of interest performed by the display controlling function 154 according to the first embodiment.

For example, let us discuss an example set with a condition as follows: "A position in the observation region corresponding to a region of interest present in a direction (the Z-direction) perpendicular to the cross-sectional plane of the observation region is displayed in red". In this situation, for example, as illustrated in FIG. 5, within the slice image S3 specified as the image of interest, the display controlling function 154 displays, in red, the pixel at (7,7,S3) being a position in the observation region corresponding to the region of interest (7,7,S1). In FIG. 5, the pixels displayed in red are indicated by the hatching pattern with diagonal lines from top left to bottom right. Also, within the slice image S3, the display controlling function 154 similarly displays, in red, the pixel at (5,5,S3) being a position in the observation region corresponding to the regions of interest (5,5,S6) and (5,5,S7). Further, within the slice image S3, the display controlling function 154 similarly displays, in red, the pixel at (4,5,S3) being a position in the observation region corresponding to the region of interest (4,5,S7) and the pixel at (4,8,S3) being a position in the observation region corresponding to the region of interest (4,8,S8). In addition, within the slice image 33, the display controlling function 154 similarly displays, in red, the pixel at (7,4,S3) being a position in the observation region corresponding to the region of interest (7,4,S5). In this situation, in the slice image S3, the pixels other than the pixels displayed with the information about the regions of interest are displayed with the original pixel values with no modification (i.e., the display of the pixels is unchanged). Further, in the example in FIG. 5, within the slice image S3, the pixel at (7,4,S3) being a position in the observation region corresponding to the region of interest (7,4,S5) has already been specified as a region of interest. In that situation, the display controlling function 154 may keep the display mode of the region unchanged.

Further, in another situation, let us discuss an example set with a condition as follows: "A position in the observation region corresponding to a region of interest present in the head direction of the directions (the Z-direction) perpendicular to the cross-sectional plane of the observation region is displayed in blue". In that situation, for example, as illustrated in FIG. 6, the pixel at (7,7,S3) being a position in the observation region corresponding to the region of interest (7,7,S1) is displayed in blue. In FIG. 6, the pixel displayed in blue is indicated by the hatching pattern with diagonal lines from top right to bottom left. Further, because the other regions of interest do not meet the condition, the display controlling function 154 does not change the display of the pixels in corresponding positions in the observation region.

Figure 7:
FIG. 7 is a drawing illustrating a specific example of the process of displaying the information about the regions of interest performed by the display controlling function according to the first embodiment.

FIG. 7 is a drawing illustrating a specific example of the process of displaying the information about the regions of interest performed by the display controlling function 154 according to the first embodiment.

For example, as illustrated in FIG. 7, when the surgery plan related to the heart valve is to be made, the display controlling function 154 causes the information about the calcification region of the heart valve to be displayed in a corresponding position in a region including the heart valve within the image of interest. For example, by using the method described above, the display controlling function 154 displays, in red and blue, the pixels in the positions corresponding to the calcification region, in a region including the heart valve within the image of interest. In FIG. 7, the pixels displayed in red are indicated by the hatching pattern with diagonal lines from top left to bottom right. The pixels displayed in blue are indicated by the hatching pattern with diagonal lines from top right to bottom left.

Further, conditions that can be used by the display controlling function 154 are not limited to the conditions described above. It is acceptable to use any condition, as long as the condition enables the judgment for causing the information corresponding to each of the regions of interest to be displayed in the observation region. For example, it is acceptable to use a condition to change the display mode of "a position in the observation region corresponding to a region of interest present in a direction at a 45-degree angle with respect to the observation cross-sectional plane". As another example, it is acceptable to use a condition to change the display mode of "a position in the observation region corresponding to a region of interest present within three pixels or less in a direction (the Z-directions) perpendicular to the cross-sectional plane of the observation region".

In the above example, as the display mode of the information about the regions of interest, the display controlling function 154 is configured to use the blue and red colors; however, it is also acceptable to use the pixel values of the regions of interest without any change. It is also acceptable to make it possible to view information about the original pixel value, by setting a degree of transparency. In another example, the display controlling function 154 may express the information about the regions of interest, by using textures or patterns, instead of the colors.

The processing functions of the processing circuitry 150 included in the medical image display apparatus 100 have thus been explained. In this situation, for example, the processing circuitry 150 is realized by using a processor. In that situation, for example, the processing functions described above are stored in the storage 120 in the form of computer-executable programs. Further, the processing circuitry 150 realizes the functions corresponding to the programs by reading and executing the programs stored in the storage 120. In other words, the processing circuitry 150 that has read the programs have the processing functions illustrated in FIG. 1.

Figure 8:
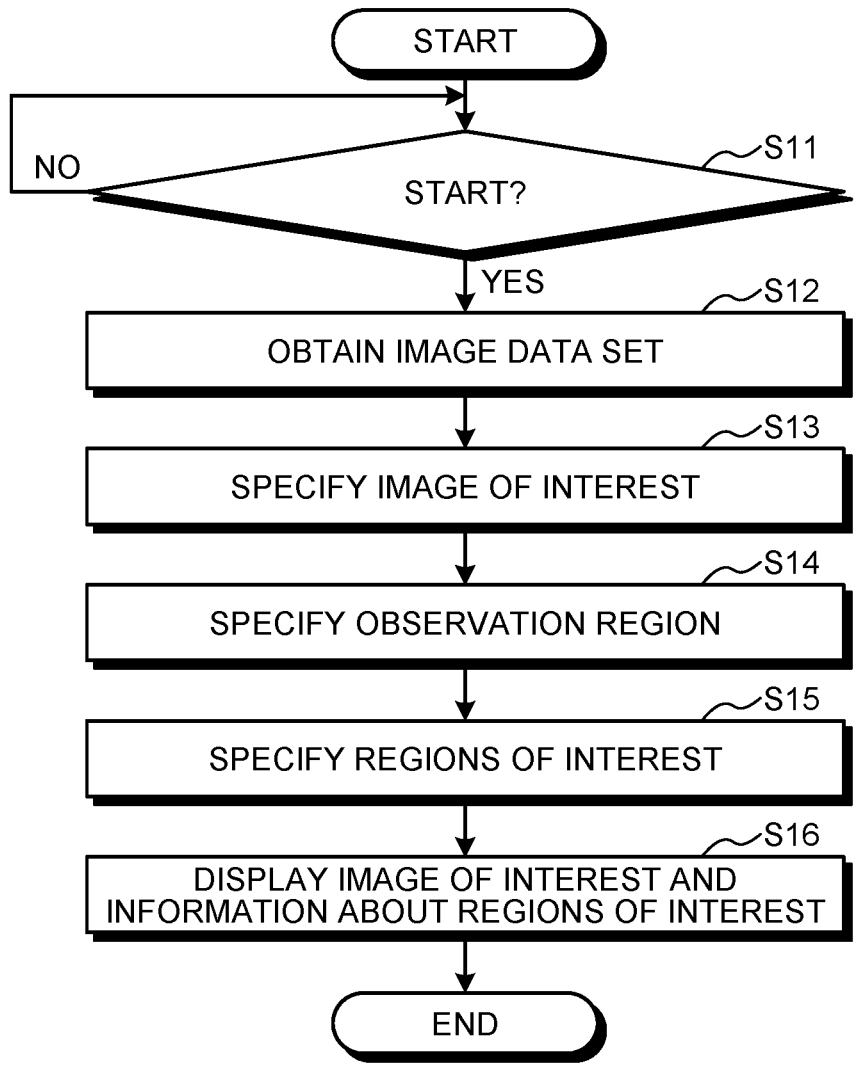
FIG. 8 is a flowchart illustrating a processing procedure in a process performed by processing circuitry included in the medical image display apparatus according to the first embodiment.

FIG. 8 is a flowchart illustrating a processing procedure in a process performed by the processing circuitry 150 included in the medical image display apparatus 100 according to the first embodiment.

For example, as illustrated in FIG. 8, when having received an instruction to start from the user via the input interface 130 (step S11: Yes), the processing circuitry 150 obtains the image data set of the volume data of the patient from either the X-ray CT apparatus 1 or the medical image storage apparatus 2 via the NW interface 110 (step S12). This step is a step corresponding to the obtaining function 151. For example, the processing circuitry 150 performs this step by reading and executing the program corresponding to the obtaining function 151 from the storage 120.

Subsequently, the processing circuitry 150 specifies an image of interest indicating an observation cross-sectional plane from the image data set of the volume data (step S13) and further specifies an observation region from the image of interest (step S14). This step is a step corresponding to the first specifying function 152. For example, the processing circuitry 150 performs this step by reading and executing the program corresponding to the first specifying function 152 from the storage 120.

After that, the processing circuitry 150 specifies regions of interest on the basis of the image data set of the volume data (step S15). This step is a step corresponding to the second specifying function 153. For example, the processing circuitry 150 performs this step by reading and executing the program corresponding to the second specifying function 153 from the storage 120.

Subsequently, the processing circuitry 150 causes the display 140 to display the image of interest and the information about the regions of interest (step S16). This step is a step corresponding to the display controlling function 154. For example, the processing circuitry 150 performs this step by reading and executing the program corresponding to the display controlling function 154 from the storage 120.

In this situation, the processing circuitry 150 does not necessarily have to be realized by using a single processor and may be structured by combining together a plurality of independent processors, so that the processing functions are realized as a result of the processors executing the programs. Further, the processing functions of the processing circuitry 150 may be realized as being distributed among or integrated into one or more pieces of processing circuitry, as appropriate. Further, the processing functions of the processing circuitry 150 may be realized by a combination of hardware (i.e., circuitry) and software. Further, although the example was explained above in which the programs corresponding to the processing functions are stored in the single storage (i.e., the storage 120), possible embodiments are not limited to this example. For instance, the programs corresponding to the processing functions may be stored in a plurality of storages in a distributed manner, so that the processing circuitry 150 reads and executes the programs from the storages. Further, the software to realize the processing functions may operate in a server connected via a network such as a cloud.

As explained above, in the first embodiment, the obtaining function 151 is configured to obtain the image data set of the volume data from either the X-ray CT apparatus 1 or the medical image storage apparatus 2. Further, the first specifying function 152 is configured to specify the image of interest indicating the observation cross-sectional plane from the image data set of the volume data. Further, on the basis of the image data set of the volume data, the second specifying function 153 is configured to specify the regions of interest. Further, the display controlling function 154 is configured to cause the display 140 to display the image of interest and the information about the regions of interest.

With this configuration, by specifying the regions of interest on the basis of the image data set, such as the volume data, that has the information in the direction orthogonal to the observation cross-sectional plane and by causing the information about the regions of interest to be displayed, it is possible to present the user with the information about the regions of interest that are present in locations other than on the observation cross-sectional plane. Accordingly, when making a surgery plan, the user such as a medical doctor is able to recognize the information about the regions of interest more accurately.

For example, when the surgery plan related to the heart valve is to be made, the medical image display apparatus 100 is configured to specify the calcification region of the heart valve on the basis of the image data set of the volume data and to cause the display 140 to display the information about the calcification region together with the image of interest. With this arrangement, it is possible to display, on the observation cross-sectional plane, the information about the position and the amount of the calcification that is present in the locations other than on the observation cross-sectional plane, in an easy-to-understand manner. As a result, the user such as a medical doctor is able to recognize the information about the calcification of the target site on the observation cross-sectional plane more accurately and to perform measuring and estimating processes more accurately.

Consequently, according to the first embodiment, it is possible to assist the process of making the surgery plan more appropriately.

First Modification Example of First Embodiment

In the first embodiment above, the example was explained in which the display controlling function 154 is configured to display the pieces of information about the different regions of interest in mutually the same display mode (e.g., in red or blue), on the basis of the condition set in advance; however, possible methods for displaying the information about the regions of interest are not limited to this example.

For instance, the display controlling function 154 may control the display mode of the pieces of information about the different regions of interest, on the basis of a condition (hereinafter, "second condition") set in advance separately from the abovementioned condition.

For example, the display controlling function 154 may be configured to control the display mode of the information about the regions of interest, on the basis of one of the following: a spatial or temporal distance between the information about the region of interest to be projected onto the image of interest and the image of interest; and a positional relationship between the information about the region of interest to be projected onto the image of interest and the image of interest.

In another example, the display controlling function 154 may be configured to control the display mode of the information about the regions of interest being projected onto the image of interest, on the basis of the pixel values of the information about the regions of interest.

In one example, the display controlling function 154 may be configured to change the display mode of the information about the regions of interest, for instance, in accordance with the distance from the observation cross-sectional plane.

Figure 9:
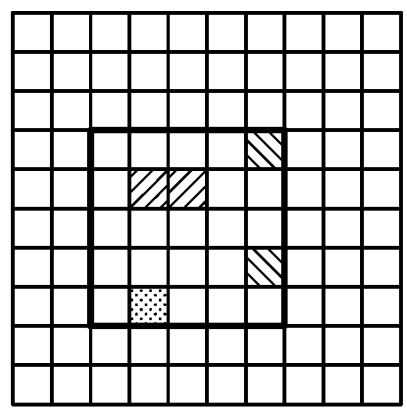
FIG. 9 is a drawing illustrating an example of a process of displaying information about regions of interest performed by a display controlling function according to a first modification example of the first embodiment.

FIG. 9 is a drawing illustrating an example of the process of displaying the information about regions of interest performed by the display controlling function 154 according to a first modification example of the first embodiment.

For example, let us discuss an example set with a condition, which serves as the second condition, as follows: "When a region of interest is distant from the observation cross-sectional plane by 1 or 2 slices, the display is in red; when being distant by 3 or 4 slices, the display is in blue; and when being distant by 5 or more slices, the display is in green". In that situation, as for the regions of interest (7,7,S1) and (7,4,S5) illustrated in FIG. 4, because the distance from the observation region is 2 slices, the display controlling function 154 displays, in red, the pixels at (7,7,S3) and (7,4,S3) being positions in the observation region corresponding to the regions of interest, within the slice image S3 specified as an image of interest, as illustrated in FIG. 9, for example. In FIG. 9, the pixels displayed in red are indicated by the hatching pattern with diagonal lines from top left to bottom right. Further, as for the regions of interest (5,5,S6), (5,5,S7), and (4,5,S7) illustrated in FIG. 4, because the distance from the observation region is 3 or 4 slices, the display controlling function 154 displays, in blue, the pixels at (5,5,S3) and (4,5,S3) being positions in the observation region corresponding to the regions of interest, within the slice image S3. In FIG. 9, the pixels displayed in blue are indicated by the hatching pattern with diagonal lines from top right to bottom left. Further, as for the region of interest (4,8,S8) illustrated in FIG. 4, because the distance from the observation region is 5 slices, the display controlling function 154 displays, in green, the pixel at (4,8,S3) being a position in the observation region corresponding to the region of interest, within the slice image S3. In FIG. 9, the pixel displayed in green is indicated by a dotted pattern.

Further, in another example, the display controlling function 154 may be configured to change the display mode of the information about the regions of interest, in accordance with the number of regions of interest corresponding to positions on the observation cross-sectional plane.

Figure 10:
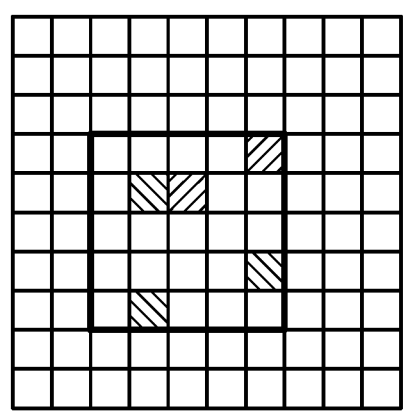
FIG. 10 is a drawing illustrating another example of the process of displaying information about regions of interest performed by the display controlling function according to the first modification example of the first embodiment.

FIG. 10 is a drawing illustrating the one other example of the process of displaying the information about the regions of interest performed by the display controlling function 154 according to the first modification example of the first embodiment.

For example, let us discuss an example set with a condition, which serves as the second condition, as follows: "When the number of regions of interest corresponding to positions in the observation region is one pixel, the display is in red; and when the number of regions of interest is two pixels, the display is in blue". In that situation, as for the regions of interest (7,7,S1), (4,5,S7) and (4,8,S8) illustrated in FIG. 4, because the number of regions of interest respectively corresponding to (7,7,S3), (4,5,S3), and (4,8,S3) being corresponding positions in the observation region within the slice image S3 specified as the image of interest corresponds only to one pixel, the display controlling function 154 displays, in red, each of the pixels in the positions within the observation region as illustrated in FIG. 10, for example. In FIG. 10, the pixels displayed in red are indicated by the hatching pattern with diagonal lines from top left to bottom right. Further, as for the regions of interest (7,4,S3) and (7,4,S5) and the regions of interest (5,5,S6) and (5,5,S7) illustrated in FIG. 4, because the number of regions of interest respectively corresponding to (7,4,S3) and (5,5,S3) being corresponding positions in the observation region within the slice image S3 corresponds to two pixels, the display controlling function 154 displays, in blue, each of the pixels in the positions within the observation region as illustrated in FIG. 10, for example. In FIG. 10, the pixels displayed in blue are indicated by the hatching pattern with diagonal lines from top right to bottom left.

In another example, the display controlling function 154 may be configured to change the display mode of the information about the regions of interest, in accordance with the pixel values of the regions of interest.

For example, let us discuss an example set with a condition, which serves as the second condition, as follows: "When the pixel value of a region of interest is equal to or larger than a threshold value, the display is in red; and when the pixel value thereof is smaller than the threshold value, the display is in blue". In that situation, when a plurality of regions of interest correspond to a position in the observation region, the display controlling function 154 is configured to use an average value, a maximum value, or a total value of the pixel values of the plurality of regions of interest, as the pixel value in the abovementioned condition.

Possible examples of the second condition are not limited to the condition described above. It is acceptable to use any condition, as long as it is possible to recognize the information corresponding to each of the regions of interest on the basis of the specific condition.

For example, in the example above, the display mode is changed by assigning the colors in correspondence with the discrete conditional analyses of the situations. However, when a condition is set with a factor having continuous values such as the distance from the observation cross-sectional plane, the number of regions of interest, and the pixel values, the second condition may be set so as to continuously change the display mode. For example, it is acceptable to set the second condition so that, while a 255-level grayscale is used, colors are continuously assigned in accordance with the length of the distances in such a manner that the closer a region of interest is positioned to the observation cross-sectional plane, the whiter color is assigned; and the farther a region of interest is positioned from the observation cross-sectional plane, the darker color is assigned. Alternatively, the second condition may be set so as to continuously change the degree of transparency.

In yet another example, the second condition may be set so as to change the display mode in accordance with positional relationships between the observation cross-sectional plane and the regions of interest. For example, the second condition may be set in such a manner that, when a region of interest is present in a slice image (the slice image S1 or S2 in FIG. 4) positioned in the head direction with respect to the observation cross-sectional plane, a pixel in the corresponding position on the observation cross-sectional plane is displayed in a reddish color, whereas when a region of interest is present in a slice image (any one of the slice images S4 to S8 in FIG. 4) positioned in the toe direction, a pixel in the corresponding position on the observation cross-sectional plane is displayed in a blueish color.

Further, for example, it is acceptable to set, as the second condition, a condition obtained by combining together two or more of the plurality of conditions described above. For example, it is acceptable to set the second condition, by combining a plurality of conditions together as follows: "When a region of interest is distant from the observation cross-sectional plane by 1 or 2 slices, while the pixel value of the region of interest is equal to or larger than a threshold value, the display is in green". In another example, it is also acceptable to set a condition of "not being displayed" as the second condition as follows: "When a region of interest satisfies both of the conditions of being distant from the observation cross-sectional plane by 2 or more slices and having a pixel value smaller than a threshold value, the region of interest is not displayed on the observation cross-sectional plane".

Further, the second condition of the various types described above may arbitrarily be set by the user through a user interface.

For example, the display controlling function 154 may be configured to receive, from the user, a condition related to at least one of: the distance from the observation cross-sectional plane, the number of regions of interest corresponding to positions on the observation cross-sectional plane, and the pixel values of the regions of interest, so as to change the display mode of the information about the regions of interest on the basis of the received condition.

For example, the display controlling function 154 may be configured to cause the display 140 to display a setting-purpose screen used for inputting setting values related to the second condition so as to receive the condition from the user.

FIG. 11 is a drawing illustrating an example of the setting-purpose screen displayed by the display controlling function 154 according to the first modification example of the first embodiment.

For example, as illustrated in FIG. 11, the display controlling function 154 causes the display 140 to display the setting-purpose screen including: checkboxes used for selecting one or more from among the three conditions such as the distance from the observation cross-sectional plane, the pixel value of the region of interest (a total when there are more than one), and the number of regions of interest; text boxes used for inputting setting values of the conditions; and checkboxes used for selecting whether the one or more regions of interest satisfying the selected condition are to be displayed or not.

User interfaces that can be used for setting the second condition are not limited to the setting-purpose screen illustrated in FIG. 11. It is acceptable to use any interface as long as the user is able to set the abovementioned conditions. For example, the user interface used for setting the second condition may be an interface that allows a complicated condition to be set by accepting an input of various types of logical expressions (AND, OR, NOT, etc.). Further, for example, the interface may be configured to allow the user to set, as appropriate, a display mode (color, texture, pattern, etc.) to be used at the time of having the information about the regions of interest displayed, with respect to each of the various conditions.

Second Modification Example of First Embodiment

Further, in the first embodiment above, the example was explained in which, after the first specifying function 152 has specified the image of interest and the observation region, the second specifying function 153 specifies the regions of interest, so that the display controlling function 154 displays the information about the regions of interest; however, the timing with which the information about the regions of interest is displayed is not limited to the one in this example.

For example, another arrangement is acceptable in which, after the obtaining function 151 obtains the image data set of the volume data, the second specifying function 153 specifies regions of interest on the basis of the image data set, so that the first specifying function 152 specifies an image of interest and an observation region with timing instructed by the user, and the display controlling function 154 displays the information about the regions of interest.

In that situation, the second specifying function 153 specifies the regions of interest on the basis of the entirety of the image data set, instead of specifying the regions of interest on the basis of the data that is included in the image data set of the volume data and corresponds to the observation region specified by the first specifying function 152. Further, of the regions of interest specified by the second specifying function 153, the display controlling function 154 displays only the information about certain regions of interest of which the corresponding positions in the image of interest are included in the observation region specified by the first specifying function 152.

With this arrangement, it is possible to cause the information about the regions of interest to be displayed, with the arbitrary timing selected by the user.

Further, for example, the display controlling function 154 may be configured to forward images from one slice to another or to change enlargement ratios, as a result of the user performing an operation called browsing on the image displayed on a display screen of the display 140. In the present example, in response to the operation, the observation region specified by the first specifying function 152 changes. In that situation, the display controlling function 154 may be configured to update regions related to the regions of interest every time the user performs the operation or may be configured to switch between displays of the information about the regions of interest according to instructions from the user.

Second Embodiment

Next, a second embodiment will be explained. In the following sections, the second embodiment will be explained while a focus is placed on differences from the first embodiment. As for some of the characteristics that are the same as those in the first embodiment, detailed explanations thereof will be omitted.

In the first embodiment described above, the display controlling function 154 is configured to cause the information about the regions of interest to be displayed. In contrast, in the second embodiment, the display 140 is caused to display information about regions of interest in a closed region that at least partially includes the regions of interest.

For example, when the surgery plan related to the heart valve is to be made, the display controlling function 154 is configured to cause an image of interest and information about a calcification region within a closed region that at least partially includes the calcification region to be displayed.

For example, the display controlling function 154 is configured to automatically measure a predetermined measurement item, by using the regions of interest specified by the second specifying function 153 and to cause a measurement value obtained through the measuring process to be displayed together with the image of interest. For example, the display controlling function 154 measures (counts) the number of pixels of the regions of interest positioned on the inside of a circular cylinder of which the center is at the center of the observation region specified by the first specifying function 152 and of which the radius is arbitrarily set and further causes the counted number of pixels to be displayed together with the image of interest. In this situation, the inside of the circular cylinder is an example of the closed region. Further, the number of pixels of the regions of interest positioned on the inside of the circular cylinder is an example of the information about the calcification region within the closed region.

Figure 12:
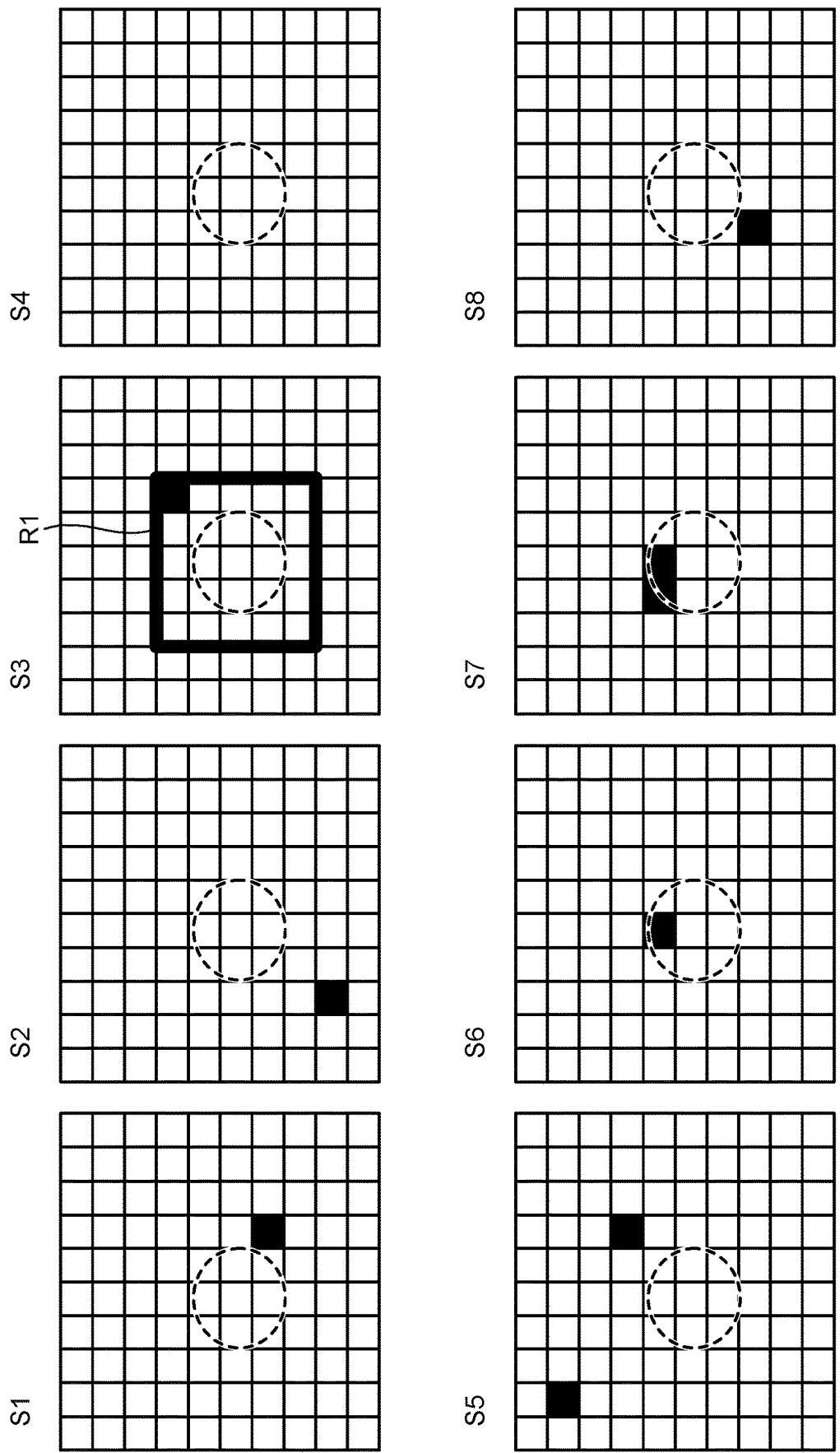
FIG. 12 is a drawing illustrating an example of a process of displaying information about a closed region performed by a display controlling function according to a second embodiment.

FIG. 12 is a drawing illustrating an example of the process of displaying the information about the closed region performed by the display controlling function 154 according to the second embodiment.

For example, as illustrated in FIG. 12, in the example illustrated in FIG. 4, the display controlling function 154 sets the pixel at (5,6,S3) positioned at the center of the observation region (the region R1 indicated with the bold frame in FIG. 4) as the center, further sets 1.5 pixels as the radius, and sets the slice image S1 and the slice image S8 as the bases of the circular cylinder. These settings may arbitrarily be established by the user through a user interface or may be set in advance. In another example, these settings may automatically be established in accordance with the size of the observation region or a distribution of the regions of interest.

In FIG. 12, the circumference of the circle corresponding to the surface of the circular cylinder being set is indicated with a broken line in each of the slice images S1 to S8. In the present example, the pixels that are partially or entirely included in the inside of the circumference are (5,5,S6), (4,5,S7), and (5,5,S7). Accordingly, the display controlling function 154 displays "3" as the number of pixels of the regions of interest that are present on the inside of the circular cylinder. In this situation, for example, with respect to a pixel such as the one at (4,5,S7) that is only partially included in the inside of the circumference, the display controlling function 154 may use a converted value corresponding to the ratio of how much is included in the inside of the circumference. For example, when the ratio of the pixel at (4,5,S7) being included in the inside of the circumference is 0.6, the display controlling function 154 may display "2.6" as the number of pixels of the regions of interest that are present on the inside of the circular cylinder.

In this situation, the shape of the closed region set as the range of the measuring process is not limited to a circular cylinder and may have any shape. For example, the shape of the closed region may be a shape similar to that of the observation region so as to fit the shape of the observation region or may be a sphere or a rectangular cylinder. In another example, the observation region itself (i.e., the entire observation region) may be set as a closed region subject to the measuring process.

Further, the value serving as a measurement item may be any value as long as the value serves as the information about the region of interest. For example, instead of the number of pixels, a total value of the pixel values of the regions of interest may be used, or a combined vector may be calculated from vectors extending from the center to the regions of interest. When vector quantities are calculated, the display controlling function 154 may visualize the magnitude and the direction of each vector, by using a symbol such as an arrow within the image of interest.

Further, the display controlling function 154 may receive, from the user, a condition related to one or both of the number of regions of interest and the pixel values of the regions of interest, so as to set and display a closed region on the basis of the received condition.

In that situation, for example, the display controlling function 154 may, while using the center of the observation region as the center, calculate the circumference observed at the time when the number of pixels of the regions of interest present on the inside of a circular cylinder becomes equal to the number of pixels received from the user.

Figure 13:
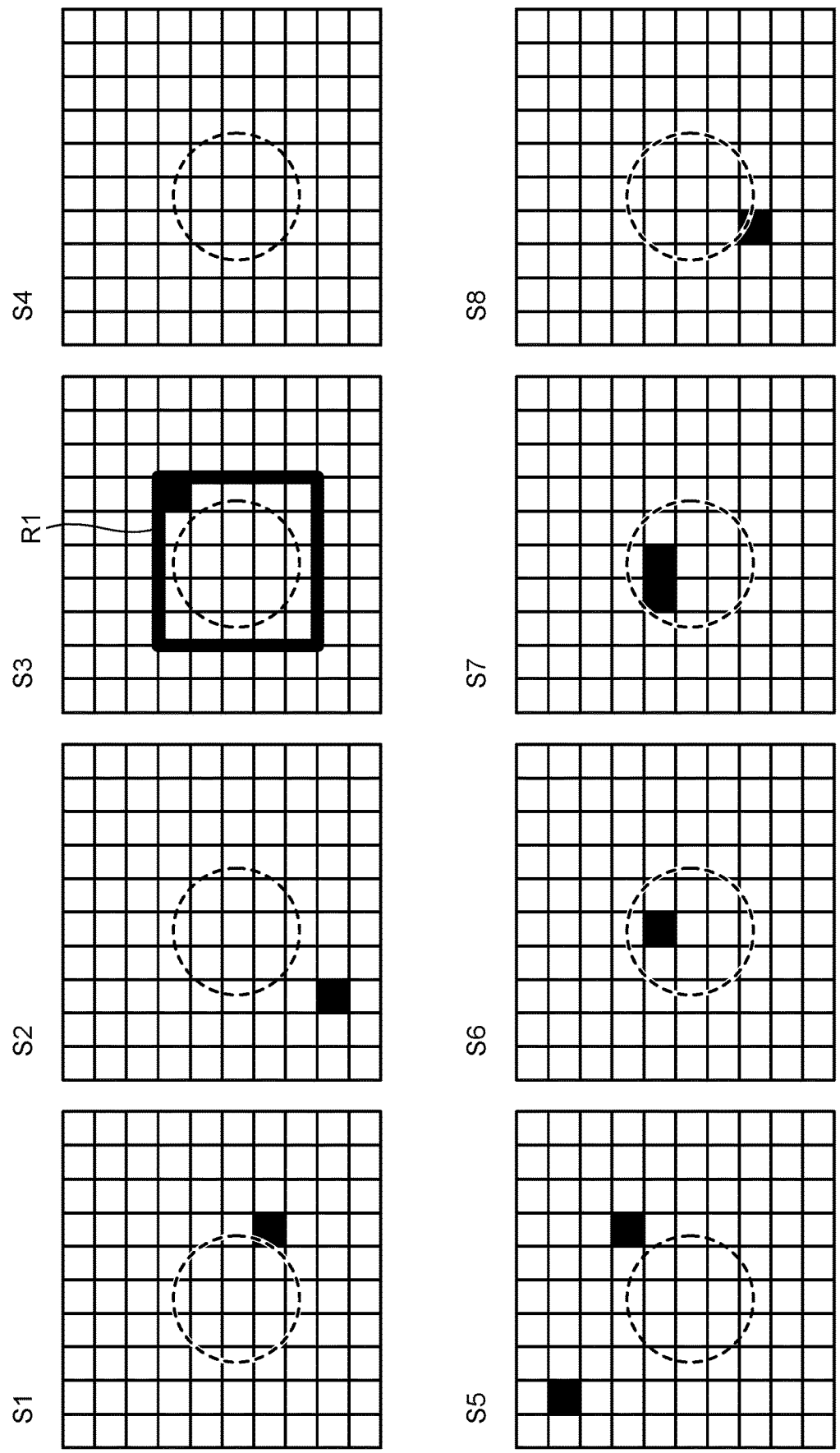
FIG. 13 is a drawing illustrating another example of the process of displaying the information about the closed region performed by the display controlling function according to the second embodiment.

FIG. 13 is a drawing illustrating another example of the process of displaying the information about the closed region performed by the display controlling function 154 according to the second embodiment.

For example, as illustrated in FIG. 13, in the example illustrated in FIG. 4, the display controlling function 154 sets a circular cylinder by using, as the center thereof, the pixel at (5,6,S3) positioned at the center of the observation region (the region R1 indicated with the bold frame in FIG. 4). Further, the display controlling function 154 calculates the number of pixels of the regions of interest present on the inside of the circular cylinder while gradually increasing the radius of the circular cylinder so as to calculate the circumference observed at the time when the calculated number of pixels becomes equal to 3.5. These settings may arbitrarily be established by the user through a user interface or may be set in advance. For example, the user may establish the setting where the number of pixels of the regions of interest is supposed to become equal to 3.5.

In FIG. 13, the circumference of the circle corresponding to the surface of the circular cylinder observed at the time when the number of pixels of the regions of interest present inside the circular cylinder becomes equal to 3.5 is indicated with a broken line in each of the slice images S1 to S8. In the present example, with respect to each of the pixels at (5,5,S6) and (5,5,S7), because the entire pixel is included in the inside of the circular cylinder, the number of pixels for each is calculated as 1. With respect to the pixel at (4,5,S7), because 90 percent of the pixel is included in the inside of the circular cylinder, the number of pixels is calculated as 0.9. Further, with respect to each of the pixels at (7,7,S1) and (4,8,S8), because 30% of each of the pixels is included in the inside of the circular cylinder, the number of pixels for each is calculated as 0.3. In this situation, the total number of pixels is 3.5, whereas the circumference at that time corresponds to a diameter of 4. Accordingly, the display controlling function 154 calculates and displays $4\pi$ as a measurement value.

The examples was explained above in which the display controlling function 154 is configured to calculate the circumference on the basis of the number of pixels of the regions of interest present on the inside of the circular cylinder; however, it is also acceptable to calculate a circumference on the basis of the pixel values. In another example, the display controlling function 154 may calculate a circumference on the basis of a value obtained by multiplying each of the pixel values by a weight corresponding to the distance from the center.

Further, the value calculated as the measurement value may be any type of value. For example, the measurement value may be the length of the diameter of the circular cylinder or may be the area of the circle or the volume of the circular cylinder.

In the present embodiment, the display controlling function 154 may cause the information (e.g., the broken lines in the examples in FIGS. 12 and 13) indicating the closed region being set as the range of the measuring process to be displayed in the image of interest, but does not necessarily have to. Further, according to an instruction from the user, the display controlling function 154 may switch between a displayed state and a non-displayed state of the information indicating the closed region.

Further, in the present embodiment, the display controlling function 154 may further cause the information about the closed region described above to be displayed in addition to the information about the regions of interest explained in the first embodiment or may cause the information about the closed region to be displayed in place of the information about the regions of interest.

As explained above, in the second embodiment, the display controlling function 154 is configured to cause the information about the regions of interest in the closed region that at least partially includes the regions of interest to be displayed.

With this arrangement, when making a surgery plan, the user such as a medical doctor is able to easily recognize the closed region including the regions of interest that satisfy the specific index (e.g., a quantity).

Consequently, according to the second embodiment also, it is possible to assist the process of making the surgery plan more appropriately.

Modification Examples of Second Embodiment

In the second embodiment described above, the display controlling function 154 is configured to cause the information about the regions of interest to be displayed; however, it is also acceptable to further display important information other than the information about the regions of interest.

For example, when an observed site is the aortic valve, the display controlling function 154 may be configured to extract the contour of the aorta from an image data set of volume data and to further cause information indicating the contour to be displayed in an image of interest.

In another example, the display controlling function 154 may be configured to extract the aortic annulus from an image data set of volume data and to further cause information indicating the aortic annulus to be displayed in an image of interest, together with the diameter of the annulus.

Figure 14:
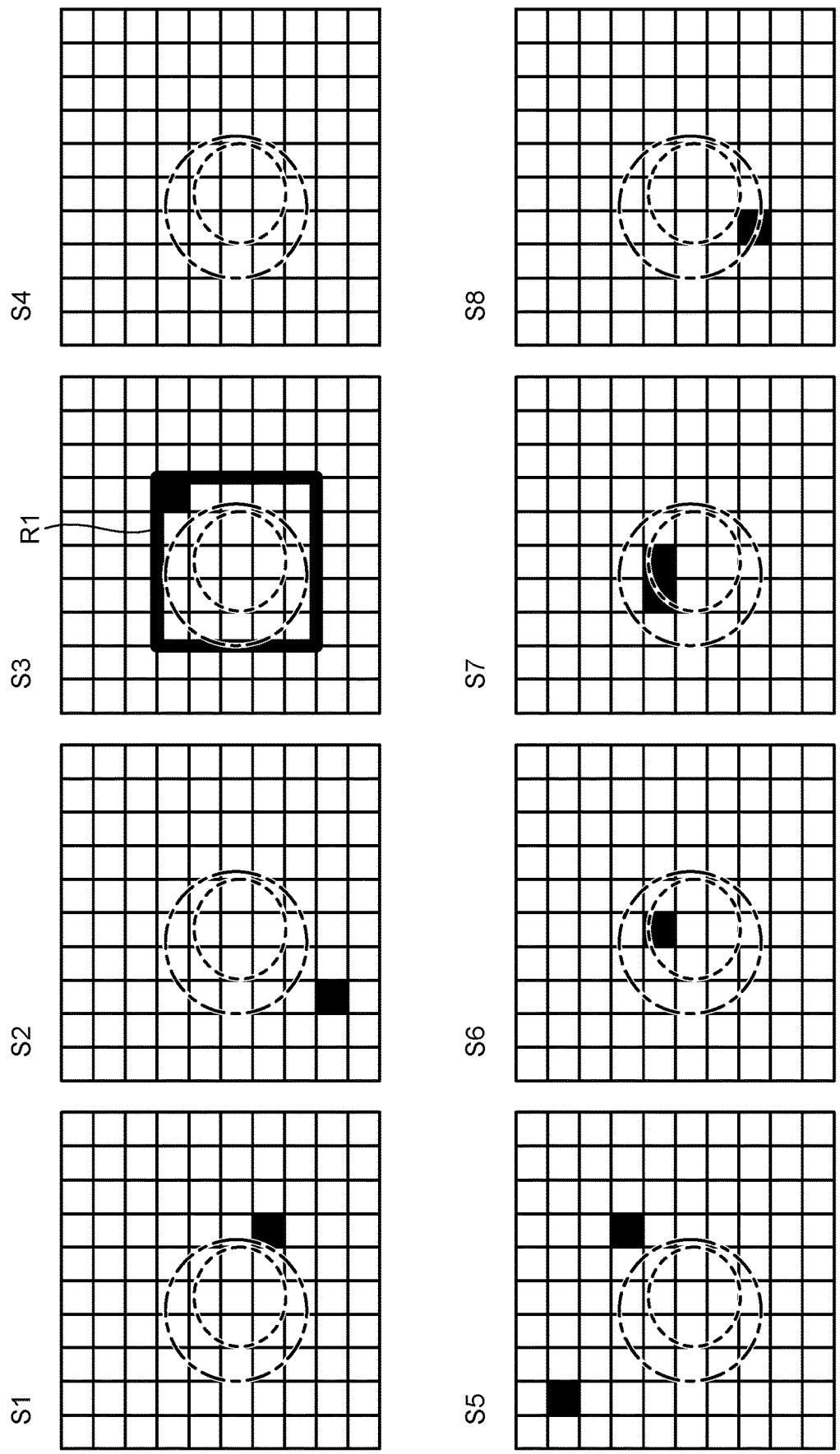
FIG. 14 is a drawing illustrating an example of a process of displaying information indicating an aortic annulus performed by a display controlling function according to a first modification example of the second embodiment.

FIG. 14 is a drawing illustrating an example of the process of displaying the information indicating the aortic annulus performed by the display controlling function 154 according to a first modification example of the second embodiment.

For example, as illustrated in FIG. 14, the display controlling function 154 displays, in addition to the information illustrated in FIG. 12, the information indicating the contour of the aortic annulus, in the slice image S3 specified as the image of interest. In FIG. 14, the information indicating the contour of the aortic annulus displayed by the display controlling function 154 is indicated by a one-dotted chain line. FIG. 14 illustrates the example in which the information indicating the contour of the aortic annulus is displayed while being projected onto each of the slice images.

With this arrangement, on the observation cross-sectional plane, it is possible to evaluate impacts of the regions of interest with a higher level of precision.

Modification Examples of First and Second Embodiments

In the first and the second embodiments described above, the examples were explained in which the surgery plan related to the heart valve is made; however, anatomical structures that can be used in the present embodiments are not limited to heart valves.

For example, when a surgery plan related to a coronary artery is to be made, the second specifying function 153 may be configured to specify the position of plaque in the coronary artery as a region of interest, so that the display controlling function 154 causes information about the specified plaque to be displayed on an observation cross-sectional plane. In that situation, the display controlling function 154 may be configured to change the display mode of the information in accordance with the density or the size of the plaque.

In another example, when a surgery plan related to an anatomical structure including a plurality of blood vessels is to be made, the user may wish to understand relationships between an observation cross-sectional plane and the positions of the blood vessels in terms of the direction of the observation cross-sectional plane. In that situation, the second specifying function 153 may be configured to specify the position of a primary blood vessel as a region of interest, so that the display controlling function 154 causes information about the specified primary blood vessel to be displayed on an observation cross-sectional plane.

In yet another example, when a treatment plan related to radiotherapy is to be made, the user may wish to understand a positional relationship of other organs in terms of the radiating direction of the radiation. In that situation, the second specifying function 153 may be configured to specify, as a region of interest, the position of an important organ (e.g., the positions of the eyeballs when the brain is to be irradiated) present in the radiation direction, so that the display controlling function 154 causes information about the specified important organ to be displayed on a cross-sectional plane corresponding to the radiation field.

Third Embodiment

Next, a third embodiment will be explained. In the following sections, the third embodiment will be explained while a focus is placed on differences from the first embodiment. As for some of the characteristics that are the same as those in the first embodiment, detailed explanations thereof will be omitted.

In the first embodiment described above, the medical image display apparatus 100 is configured to display the information about the regions of interest on the basis of the image data set of the volume data at a single point in time. In the third embodiment, the information about the regions of interest is displayed on the basis of image data set of image data at multiple points in time.

More specifically, the obtaining function 151 is configured to obtain the image data set of the image data of the patient at the multiple points in time, from either the X-ray CT apparatus 1 or the medical image storage apparatus 2, via the NW interface 110. In this situation, the image data at the multiple points in time represent CT images taken by the X-ray CT apparatus 1.

For example, during medical examinations of the heart or the lungs, images at multiple points in time are taken in the time-axis direction in a medical examination at each time, by using an imaging method called four-dimensional (4D) imaging. For example, the obtaining function 151 is configured to obtain the image data set of the images at the multiple points in time taken in this manner. In another example, when a single image is taken in a medical examination at each time, but medical examinations are performed multiple times so as to continue with regular follow-up observations, the obtaining function 151 may be configured to obtain an image data set of images at multiple points in time taken over the medical examinations performed at the different times.

Figure 15:
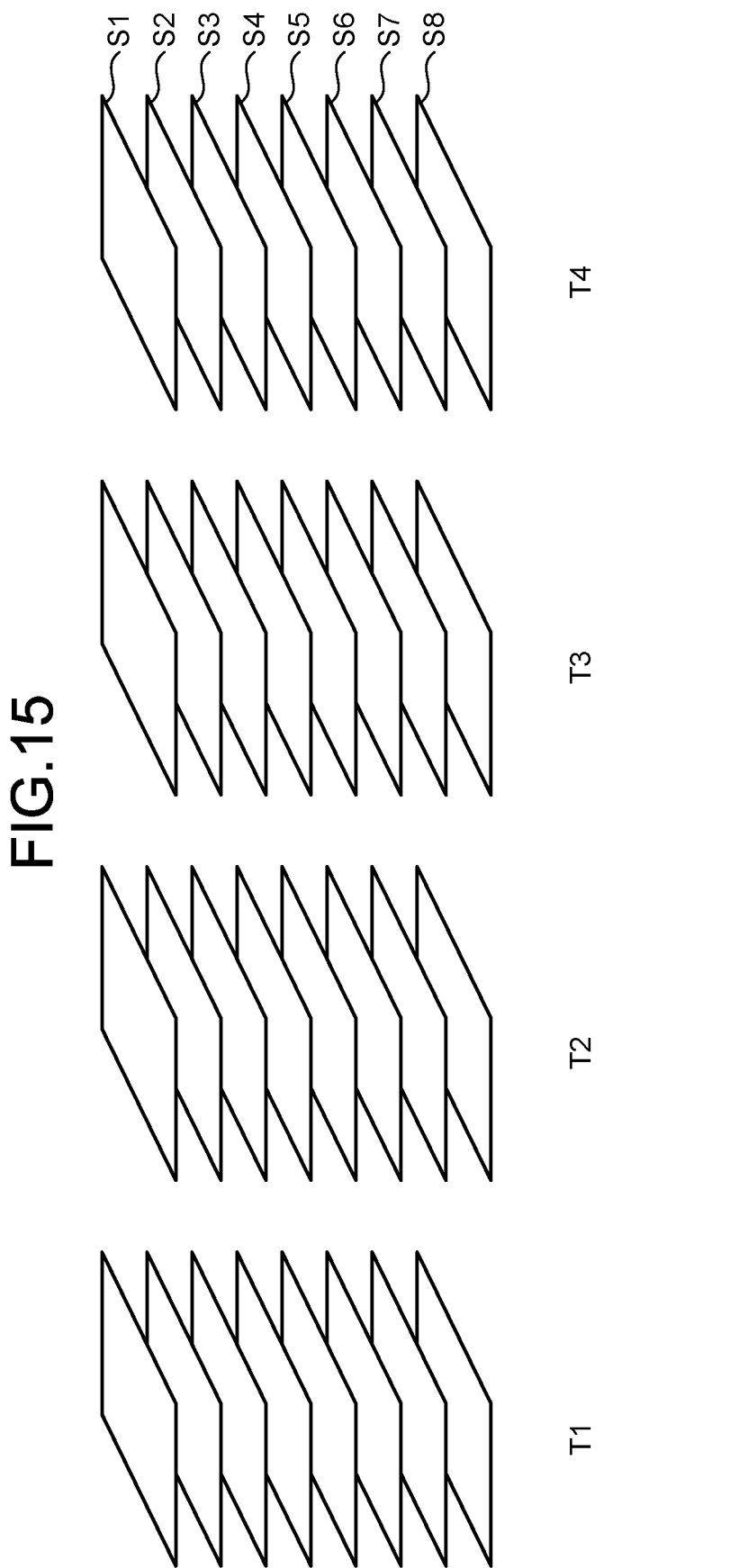
FIG. 15 is a drawing illustrating an example of an image data set of image data at multiple points in time obtained by an obtaining function according to a third embodiment.

FIG. 15 is a drawing illustrating an example of the image data set of the image data at the multiple points in time obtained by the obtaining function 151 according to the third embodiment.

For example, as illustrated in FIG. 15, in the present embodiment, let us discuss an example in which the obtaining function 151 has obtained the image data set including pieces of volume data at four points in time T1 to T4, while each of the pieces of volume data includes eight slice images S1 to S8 that are sequentially arranged in the head-to-toe direction. In this situation, let us assume that the slice images included in each of the pieces of volume data includes pixels arranged as ten pixels in the X-direction by ten pixels in the Y-direction, similarly to the first embodiment.

The first specifying function 152 is configured to specify an image of interest indicating an observation cross-sectional plane, from the image data set of the image data at the multiple points in time obtained by the obtaining function 151. Also, the first specifying function 152 is configured to further specify an observation region from the image of interest. In this situation, the method used by the first specifying function 152 to specify the image of interest and the observation image is the same as the method described in the first embodiment.

Figure 16:
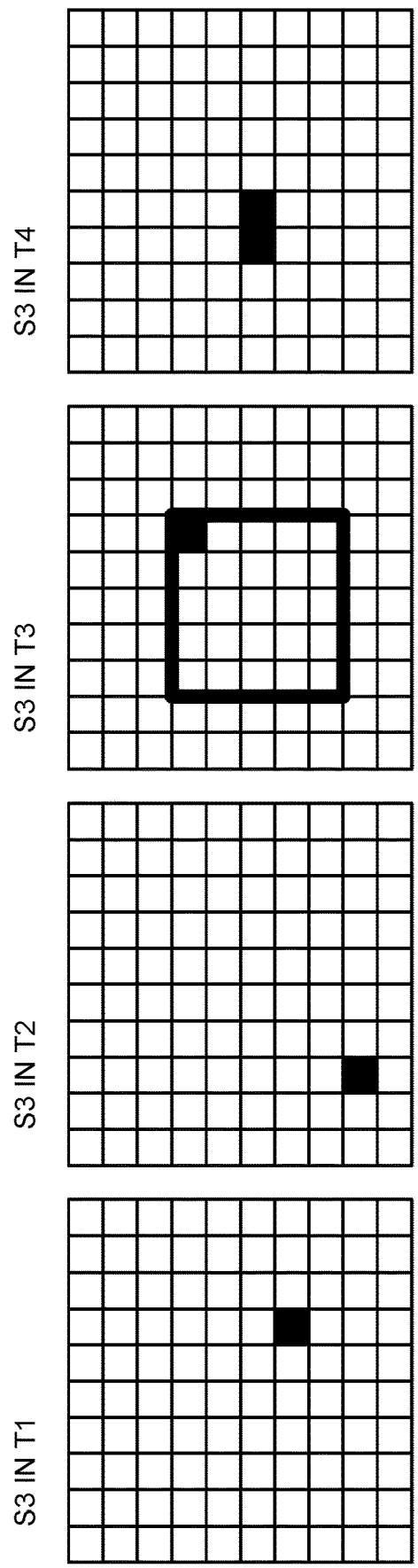
FIG. 16 is a drawing illustrating an example of a process of specifying an image of interest and an observation region performed by a first specifying function according to the third embodiment.

FIG. 16 is a drawing illustrating an example of the process of specifying the image of interest and the observation region performed by the first specifying function 152 according to the third embodiment.

For example, as illustrated in FIG. 16, in the present embodiment, let us assume that the first specifying function 152 has specified, as the image of interest, the slice image S3 at the point in time T3, from the image data set of the pieces of volume data at the points in time T1 to T4 illustrated in FIG. 15. Further, let us assume that the first specifying function 152 has specified, as the observation region (the region indicated with the bold frame in FIG. 16), a region corresponding to the range with the X coordinates of 3 to 7 and the range with the Y-coordinates of 4 to 8 in the slice image S3 specified as the image of interest. To simplify the explanation, FIG. 16 illustrates only the slice images S3 at the different points in time.

The second specifying function 153 is configured to specify regions of interest on the basis of the image data set of the image data at the multiple points in time obtained by the obtaining function 151. In this situation, the second specifying function 153 is configured to specify the regions of interest, on the basis of data that is included in the image data set of the volume data and corresponds to the observation region specified by the first specifying function 152. The method used by the second specifying function 153 to specify the regions of interest is the same as the method described in the first embodiment.

More specifically, in the present embodiment, the second specifying function 153 obtains a region of interest from each of the pieces of volume data at the multiple points in time. For instance, let us discuss an example in which the regions corresponding to the positions of the black pixels in FIG. 16 have been specified as the regions of interest. In other words, in FIG. 16, the second specifying function 153 has specified, as the regions of interest, (7,7,S3) in the slice image S3 at the point in time T1, (3,9,S3) in the slice image S3 at the point in time T2, (7,4,S3) in the slice image S3 at the point in time T3, and (4,6,S3) and (5,6,S3) in the slice image S3 at the point in time T4. To simplify the explanation, FIG. 16 illustrates the regions of interest only from the slice image S3; however, in actuality, regions of interest are specified from all the slice images.

The display controlling function 154 is configured to cause the display 140 to display the image of interest specified by the first specifying function 152 and information about the regions of interest specified by the second specifying function 153. Further, the display controlling function 154 is configured to cause the information about the regions of interest to be displayed in positions within the image of interest corresponding to the regions of interest.

More specifically, on the basis of a condition set in advance, the display controlling function 154 is configured to cause the information about each of the regions of interest in the images taken at the mutually-different points in time to be displayed in a corresponding position in the observation region within the image of interest.

Figure 17:
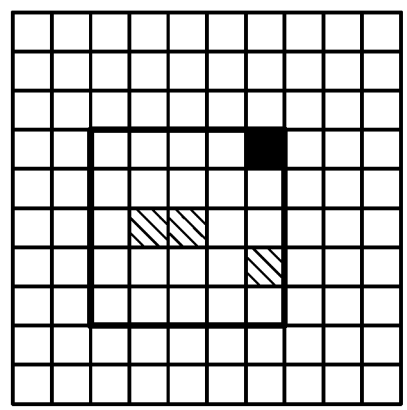
FIG. 17 is a drawing illustrating an example of a process of displaying information about regions of interest performed by a display controlling function according to the third embodiment.

FIG. 17 is a drawing illustrating an example of the process of displaying the information about the regions of interest performed by the display controlling function 154 according to the third embodiment.

For example, let us discuss an example set with a condition as follows: "In images taken at points in time other than the point in time at which the image including the observation region was taken, the positions of the regions of interest corresponding to pixels in the observation region are displayed in red". In this situation, for example, as illustrated in FIG. 17, the display controlling function 154 displays, in red, the pixel at (7,7,S3) at T3 being a corresponding position in the observation region with respect to the region of interest at (7,7,S3) in the slice image S3 at the point in time T1. Similarly, the display controlling function 154 displays, in red, the pixels at (4,6,S3) and (5,6,S3) in the slice image S3 at the point in time T3 corresponding to (4,6,S3) and (5,6,S3) in the slice image S3 at the point in time 14. In FIG. 17, the pixels displayed in red are indicated by the hatching pattern with diagonal lines from top left to bottom right. The pixels displayed in blue are indicated by the hatching pattern with diagonal lines from top right to bottom left.

The condition that can be used by the display controlling function 154 is not limited to the condition presented above. It is acceptable to use any condition as long as the condition enables the judgment for causing the information corresponding to each of the regions of interest to be displayed in the observation region.

As explained above, in the third embodiment, the obtaining function 151 is configured to obtain the image data set of the image data at the multiple points in time, from either the X-ray CT apparatus 1 or the medical image storage apparatus 2. Further, the first specifying function 152 is configured to specify the image of interest indicating the observation cross-sectional plane from the image data set of the image data at the multiple points in time. Also, the second specifying function 153 is configured to specify the regions of interest on the basis of the image data set of the image data at the multiple points in time. Furthermore, the display controlling function 154 is configured to cause the display 140 to display the image of interest and the information about the regions of interest.

With this arrangement, by specifying the regions of interest on the basis of the image data set having the information in the time-axis direction such as the pieces of image data at the multiple points in time and causing the information about the regions of interest to be displayed, it is possible to present the user with the information about the regions of interest that are present in the locations other than on the observation cross-sectional plane. Accordingly, when making the surgery plan, the user such as a medical doctor is able to recognize the information about the regions of interest more accurately.

Consequently, according to the third embodiment also, it is possible to assist the process of making the surgery plan more appropriately.

Modification Examples of Third Embodiment

In the third embodiment described above, the display controlling function 154 is configured to cause the information to be displayed with respect to the regions of interest satisfying the condition among the regions of interest in all the pieces of image data obtained by the obtaining function 151; however, it is also acceptable to cause information to be displayed only with respect to regions of interest in certain image data at a clinically important point in time.

In that situation, the first specifying function 152 is configured to further specify one or more pieces of important image data from the image data set of the image data at the multiple points in time obtained by the obtaining function 151.

Further, the display controlling function 154 is configured to cause the display 140 to display only the information about the regions of interest in the one or more pieces of important image data specified by the first specifying function 152.

For example, when a medical examination is performed on the heart, the first specifying function 152 may specify image data at a point in time corresponding to end diastole or early systole, so that the display controlling function 154 displays only information about regions of interest specified from the image data. In that situation, the first specifying function 152 may specify the point in time corresponding to end diastole or early systole, on the basis of cardiac phase information during an electrocardiogram-synchronized imaging process saved in a DICOM header as additional information or may calculate the volume of the left ventricle by using a known image processing technique so as to specify the point in time on the basis of the volume.

Further, for example, when medical examinations are performed multiple times so as to continue with regular follow-up observations, the first specifying function 152 may specify image data from the initial examination or a post-treatment examination, so that the display controlling function 154 displays only regions of interest specified from the image data.

Further, for example, the first specifying function 152 may specify the important image data, by receiving, from the user, a designation of image data from which the regions of interest are to be specified.

In the present modification example, the second specifying function 153 may be configured to specify region information only from certain image data specified by the first specifying function 152. With this arrangement, because the regions of interest are specified only from the image data at the necessary point in time, it is possible to reduce calculation costs.

Modification Examples of First and Third Embodiments

The first embodiment and the third embodiment described above may be implemented in combination.

For example, on the basis of the image data set of the pieces of the volume data at the multiple points in time, the display controlling function 154 may be configured, with respect to each of the pieces of volume data, to bring regions of interest into correspondence with a slice cross-sectional plane at other points in time corresponding to the slice cross-sectional plane at one point in time specified as an image of interest, by using the method described in the first embodiment. Further, the display controlling function 154 may be configured to display the information about the regions of interest brought into correspondence with the slice cross-sectional planes at the other points in time, so as to be kept in correspondence with the slice cross-sectional plane at the one point in time specified as the image of interest, by using the method described in the third embodiment.

Further, it is possible to apply any of the configurations of the medical image display apparatus 100 described in the above embodiments and modification examples, to a console device of a medical image diagnosis apparatus such as the X-ray CT apparatus 1 or to the medical image storage apparatus 2. In that situation, functions equivalent to the obtaining function 151, the first specifying function 152, the second specifying function 153, and the display controlling function 154 described above will be installed in processing circuitry included in the console device of the medical image diagnosis apparatus or in processing circuitry included in the medical image storage apparatus 2.

In the embodiments and the modification examples described above, the example was explained in which the obtaining unit, the first specifying unit, the second specifying unit, and the display controlling unit of the present disclosure are realized as the obtaining function, the first specifying function, the second specifying function, and the display controlling function, respectively, that are included in the processing circuitry; however, possible embodiments are not limited to this example. For instance, instead of having the functions realized as the obtaining function, the first specifying function, the second specifying function, and the display controlling function described in the embodiments, it is possible to realize the functions of the obtaining unit, the first specifying unit, the second specifying unit, and the display controlling unit of the present disclosure by using only hardware, only software, or a combination of hardware and software.

The term "processor" used in the description of the above embodiments denotes, for example, a Central Processing Unit (CPU), a Graphics Processing Unit (GPU), or circuitry such as an Application Specific integrated Circuit (ASIC) or a programmable logic device (e.g., a Simple Programmable Logic Device [SPLD], a Complex Programmable Logic Device [CPLD], or a Field Programmable Gate Array [FPGA]). In this regard, instead of saving the programs in the storage, it is also acceptable to directly incorporate the programs in the circuitry of the processors. In that situation, the processors realize the functions by reading and executing the programs incorporated in the circuitry thereof. Further, the processors according to the present embodiments do not each necessarily have to be structured as a single piece of circuitry. It is also acceptable to structure one processor by combining together a plurality of pieces of independent circuitry, so as to realize the functions thereof.

In this situation, the programs executed by the processors are provided as being incorporated, in advance, in a Read Only Memory (ROM), a storage, or the like. The programs may be provided as being recorded in a computer-readable non-transitory storage medium such as a Compact Disk Read-Only Memory (CD-ROM), a Flexible Disk (FD), a Compact Disk Recordable (CD-R), a Digital Versatile Disk (DVD), or the like, in a file in a format that is installable or executable by these devices. Further, the programs may be stored in a computer connected to a network such as the Internet so as to be provided or distributed as being downloaded via the network. For example, the programs are structured with modules including the processing functions described above. In the actual hardware, as a result of a CPU reading and executing the programs from a storage medium such as a ROM, the modules are loaded into a main storage device and generated in the main storage device.

The constituent elements of the apparatuses in the drawings of the above embodiments and modification examples are based on functional concepts. Thus, it is not necessarily required to physically configure the constituent elements as indicated in the drawings. In other words, specific modes of distribution and integration of the apparatuses are not limited to those illustrated in the drawings. It is acceptable to functionally or physically distribute or integrate all or a part of the apparatuses in any arbitrary units, depending on various loads and the status of use. Further, all or an arbitrary part of the processing functions performed by the apparatuses may be realized by a CPU and a program analyzed and executed by the CPU or may be realized as hardware using wired logic.

Furthermore, with regard to the processes explained in the above embodiments and modification examples, it is acceptable to manually perform all or a part of the processes described as being performed automatically. Conversely, by using a publicly-known method, it is also acceptable to automatically perform all or a part of the processes described as being performed manually. Further, unless noted otherwise, it is acceptable to arbitrarily modify any of the processing procedures, the controlling procedures, specific names, and various information including various types of data and parameters that are presented in the above text and the drawings.

The various types of data handled in the present disclosure are, typically, digital data.

According to at least one aspect of the embodiments described above, it is possible to assist the process of making the surgery plan more appropriately.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image display apparatus, comprising: processing circuitry configured to:

obtain an image data set of volume data;
specify an image of interest indicating an observation cross-sectional plane from the image data set;
specify a region of interest based on the image data set;
project information about the region of interest, which exists in a direction perpendicular to the observation cross-sectional plane of the image of interest, onto the image of interest; and
cause the image of interest and the projected information about the region of interest to be displayed.

2. The medical image display apparatus according to claim 1, wherein
the processing circuitry is further configured to specify an observation region from the image of interest, and
the processing circuitry is further configured to specify the region of interest based on data that is included in the image data set and that corresponds to the observation region.

3. The medical image display apparatus according to claim 1, wherein, as the information about the region of interest, the processing circuitry is further configured to cause information about a calcification region of a heart valve to be displayed.

4. A medical image display apparatus, comprising:
processing circuitry configured to:
obtain an image data set of volume data or image data at multiple points in time;
specify an image of interest indicating a cross-sectional plane including a heart valve from the image data set;
specify a calcification region of the heart valve based on data that is included in the image data set and corresponds to a region of interest including the heart valve;
project information about the calcification region, which exists in a direction perpendicular to the cross-sectional plane including the heart valve of the image of interest, onto the image of interest; and
cause the image of interest and the projected information about the calcification region to be displayed.

5. The medical image display apparatus according to claim 1, wherein the processing circuitry is further configured to cause the information about the region of interest to be displayed in a position within the image of interest corresponding to the region of interest.

6. The medical image display apparatus according to claim 1, wherein the processing circuitry is further configured to change a display mode of the information about one or more regions of interest in accordance with at least one of: a distance from the observation cross-sectional plane, a quantity of the one or more regions of interest corresponding to positions on the observation cross-sectional plane, and a pixel value of the one or more regions of interest.

7. The medical image display apparatus according to claim 6, wherein
the processing circuitry is further configured to receive, from a user, a condition related to at least one of: the distance from the observation cross-sectional plane, the quantity of the regions of interest corresponding to the positions on the observation cross-sectional plane, and the pixel value of the one or more regions of interest, and
the processing circuitry is further configured to change the display mode of the information about the one or more regions of interest, based on the received condition.

8. The medical image display apparatus according to claim 1, wherein the processing circuitry is further configured to cause information about one or more regions of interest in a closed region that at least partially includes the one or more regions of interest to be displayed.

9. The medical image display apparatus according to claim 8, wherein the information about the one or more regions of interest is information about one of:
a quantity of the regions of interest present inside the closed region, and a pixel value of the one or more regions of interest.

10. The medical image display apparatus according to claim 1, wherein
the processing circuitry is further configured to specify at least one piece of important image data from the image data set, and
the processing circuitry is further configured to cause only information about the region of interest in the at least one piece of important image data to be displayed.

11. The medical image display apparatus according to claim 1, wherein the processing circuitry is further configured to cause the information about the region of interest to be displayed while being superimposed on the image of interest.

12. The medical image display apparatus according to claim 1, wherein the processing circuitry is further configured to control a display mode of the information about the region of interest, based on one of: a spatial distance between the information about the region of interest and the observation cross-sectional plane of the image of interest, and a positional relationship between the information about the region of interest and the observation cross-sectional plane of the image of interest.

13. The medical image display apparatus according to claim 1, wherein, based on a pixel value of the information about the region of interest, the processing circuitry is further configured to control a display mode of the information about the region of interest projected onto the image of interest.

14. The medical image display apparatus according to claim 8, wherein
the processing circuitry is further configured to receive, from a user, a condition related to at least one of: a quantity of regions of interest, or a pixel value of the regions of interest, and
the processing circuitry is further configured to set and display the closed region based on the received condition.

15. The medical image display apparatus according to claim 1, wherein the volume data and the image data at the multiple points in time represent CT images.

16. The medical image display apparatus according to claim 1, wherein the processing circuitry is further configured to control a display mode of the information about the region of interest, according to the information about the region of interest and a spatial distance from the observation cross-sectional plane of the image of interest.

17. The medical image display apparatus according to claim 1, wherein the processing circuitry is further configured to control a display mode of the information about the region of interest, according to a positional relationship between the information about the region of interest and the observation cross-sectional plane of the image of interest.

18. A medical image display apparatus, comprising:
processing circuitry configured to:
obtain an image data set of image data at multiple points in time;
specify an image of interest indicating an observation cross-sectional plane from the image data set;

specify a region of interest based on the image data set; and cause information about the region of interest, which exists at a point in time different from a point in time of the image of interest, to be displayed on the image of interest.

\* \* \* \* \*